United States Patent [19]
Sintov et al.

[11] Patent Number: 5,869,529
[45] Date of Patent: Feb. 9, 1999

[54] TOPICAL PREPARATION FOR THE PREVENTION AND TREATMENT OF LESIONS AND SORES ASSOCIATED WITH A HERPES VIRUS

[75] Inventors: Amnon Sintov, Omer; Rina Uzan, Beer-Shava, both of Israel

[73] Assignee: Agis Industries (1983) Ltd., Beni Brak, Israel

[21] Appl. No.: 595,872

[22] Filed: Feb. 6, 1996

Related U.S. Application Data

[63] Continuation-in-part of Ser. No. 503,827, Jul. 18, 1995, abandoned.

[30] Foreign Application Priority Data

Jul. 20, 1994 [IL] Israel ........................................ 110380

[51] Int. Cl.⁶ ..................................................... A61K 31/20
[52] U.S. Cl. ........................................... 514/560; 514/559
[58] Field of Search ...................... 514/560, 559

[56] References Cited

U.S. PATENT DOCUMENTS 4,764,418  8/1988  Kuenn et al. ............................ 428/284
5,434,182  7/1995  Isaacs et al. ............................ 514/546

OTHER PUBLICATIONS

HCAPLUS abstract AN–1992: 201098 (EP 465423 A2) 1992.
Embase abstract 90018210, Seki, T. et al., (1989).
Embase abstract 85192137, Cooper, E. R. et al. (1985).

*Primary Examiner*—Marianne M. Cintins
*Assistant Examiner*—Minna Moezie
*Attorney, Agent, or Firm*—Darby & Darby

[57] ABSTRACT

The invention provides a topical pharmaceutical composition for the prevention and treatment of lesions and sores of the skin or mucosa associated with a herpes virus, comprising a salt of an unsaturated $C_{14-18}$ fatty acid having 1–2 double bonds as active ingredient therein, in combination with a pharmaceutically or cosmetically acceptable carrier.

1 Claim, 2 Drawing Sheets

TOPICAL PREPARATION FOR THE PREVENTION AND TREATMENT OF LESIONS AND SORES ASSOCIATED WITH A HERPES VIRUS

This application is a continuation-in-part of U.S. application Ser. No. 08/503,827, filed Jul. 18, 1995 (now abandoned).

FIELD OF THE INVENTION

The present invention relates to a topical pharmaceutical composition and to methods for the treatment of a herpes virus using the same.

More particularly, the present invention relates to a topical pharmaceutical composition for the prevention and treatment of lesions and sores of the skin or mucosa associated with a herpes virus, comprising a salt of an unsaturated $C_{14-18}$ fatty acid having 1–2 double bonds as active ingredient therein, in combination with a pharmaceutically or cosmetically acceptable carrier.

BACKGROUND OF THE INVENTION

As compared to other areas of infectious disease, antiviral therapy has rapidly advanced during the last decades. However, despite intense efforts by pharmaceutical companies, relatively few antiviral drugs are available, in contrast to the plethora of antibiotics in clinical use. There are two main reasons for the limited use of antiviral agents: (1) most drug candidates have proven too toxic in humans, and (2) the widespread use of some antiviral agents has led to emergence of drug-resistant virus strains, particularly in immunocompromised patients.

Due to the above constraints in use of antiviral agents, and following surprising results obtained and presented herewith, the present invention is meant to provide novel compositions which prevent, and/or provide, symptomatic relief of lesions and sores associated with a herpes virus, and which compositions do not require the presence of a nucleoside analogue or any other antiviral agent now in use.

More specifically, in Israel Specification 104,283 there is described and claimed an antiviral topical pharmaceutical composition for treating viral diseases of the skin or mucosa, comprising a poorly soluble antiviral nucleoside derivative dispersed in an aqueous gel carrier containing a gelling agent and a water-solubilized carboxylic or dicarboxylic acid salt. The teachings of said specification are incorporated herein by reference.

The invention described in said specification was based on the discovery that said formulation achieved better antiviral effect than the ZoviraxR ointment or cream available on the market today.

After further research and development, however, it was surprisingly discovered that the composition described in said specification, in what was thought to be a placebo and in which the soluble anti-viral nucleoside derivative, i.e., acyclovir, was absent, also achieved better effect than the ZoviraxR ointment or cream available on the market today.

It has been concluded from the research performed with the nucleoside drug and with its absence that the antiviral effect of the composition is due to the enhanced penetration of the fatty acids as salts rather than free acids. The penetration of any antiviral agent is critical for the effective treatment of herpes virus, since the replication of the virus and the vesicles eruption occur deep in the basal epidermis (*Stratum Granulosum*).

Therefore, in light of this surprising discovery, the present invention relates to a topical pharmaceutical composition for the prevention and treatment of lesions and sores of the skin or mucosa associated with a herpes virus, comprising a salt of an unsaturated $C_{14-18}$ fatty acid having 1–2 double bonds as active ingredient therein, in combination with a pharmaceutically or cosmetically acceptable carrier.

SUMMARY OF THE INVENTION

Figure 1:
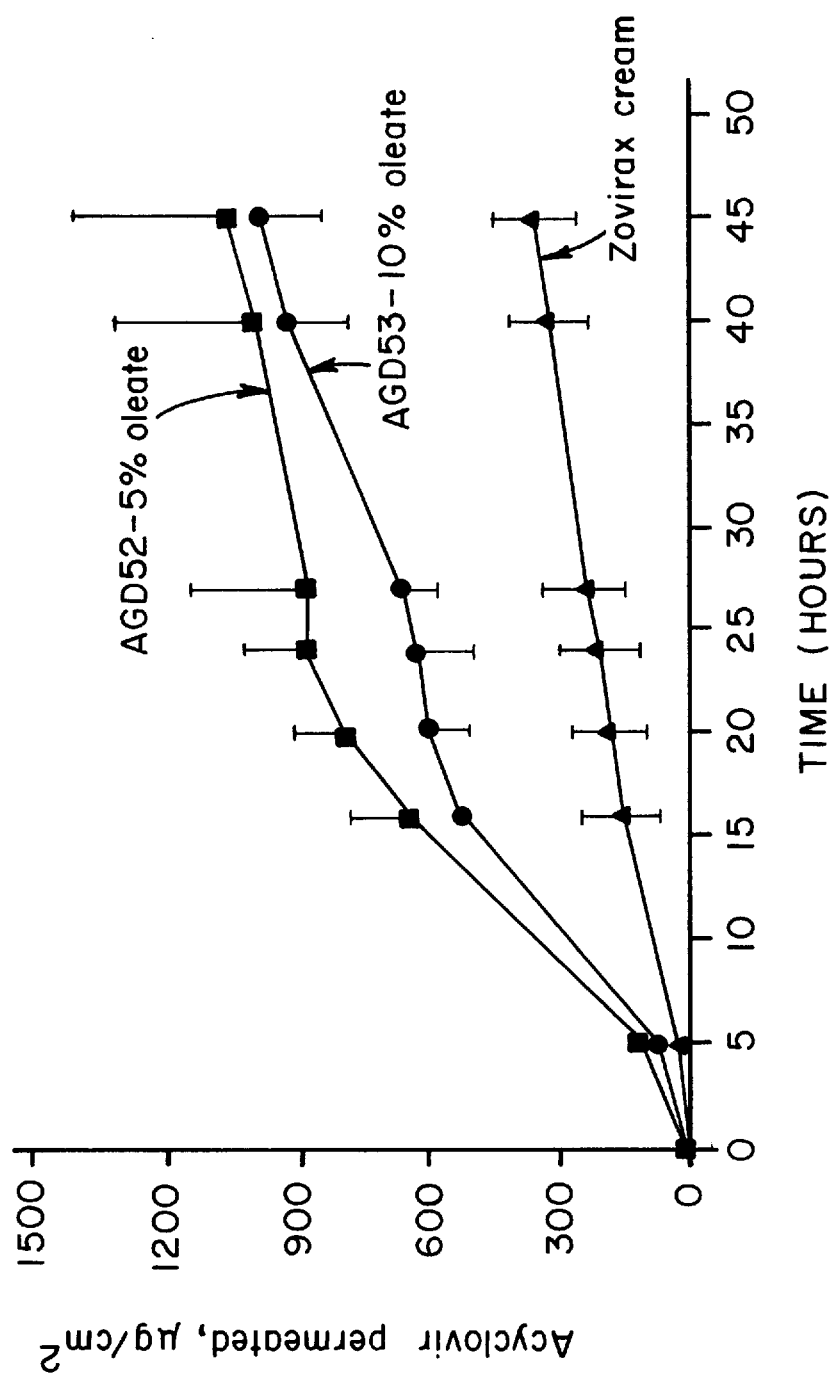
FIG. 1 is a graphic illustration of the transdermal permeation of acyclovir in mice as a function of time following administration of three different acyclovir formulations.

The present invention encompasses topical pharmaceutical compositions for the treatment of pre-existing lesions and sores of the skin or mucosa associated with a herpes virus and for prevention of future lesions and sores of the skin or mucosa associated with a herpes virus. The compositions comprise a salt of an unsaturated $C_{14-18}$ fatty acid having 1–2 double bonds as active ingredients therein, in combination with a pharmaceutically or cosmetically acceptable carrier.

The invention also encompasses methods for the treatment of pre-existing lesions and sores of the skin or mucosa associated with a herpes virus and for prevention of future lesions and sores of the skin or mucosa associated with a herpes virus, which comprise administering the above-described compositions in effective amounts for the treatment and/or prevention of these lesions.

DESCRIPTION OF THE PREFERRED EMBODIMENTS

More specifically, the present invention provides a topical pharmaceutical composition, wherein said antiviral agent is selected from the group consisting of myristoleates, linoleates, elaidates, palmitoleates and oleates. Especially preferred for use in the present invention is an alkali oleate.

Preferably, said topical composition will comprise a polyhydroxy compound selected from the group consisting of glycerine, propylene glycol, and polyethylene glycol.

Thus, the present invention, in especially preferred embodiments, provides a composition containing between about 0.1% and about 30% of a combination of alkali oleate and oleic acid, about 0 to 70% propylene glycol, and a pharmaceutically acceptable carrier. The pH of said composition is preferably adjusted to between 7 and 8.

The invention also provides a method for the prevention and treatment of lesions and sores of the skin or mucosa associated with a herpes virus, comprising administering a topical pharmaceutical composition, comprising a salt of an unsaturated $C_{14-18}$ fatty acid having 1–2 double bonds as active ingredient therein, in an effective amount for the treatment of lesions and sores of the skin or mucosa, in combination with a pharmaceutically or cosmetically acceptable carrier.

Said composition can be effective for a wide range of virus-associated and viral-like diseases. These include herpes simplex labialis, post-herpetic neuralgia, recurrent genital herpes, cancer sore, aphthous stomatitis, vulvar vestibulities, etc.

While, as indicated, it has been discovered that the above composition is effective in itself, the carboxylic acid salt of the present invention can obviously also be combined in a pharmaceutical composition with an additional poorly soluble antiviral nucleoside derivative, such as acyclovir, vidarabine, azidothymidine and ganciclovir.

The pharmaceutically or cosmetically acceptable vehicle utilizable in the compositions of the present invention can be selected from the group comprising an oil-in-water or water-in-oil emulsion, solution, cream, suspension, gel, aerosol, or powder.

Oil-in-water or water-in-oil emulsions are formulated in ways that a stable topical ointment, lotion, cream, stick or foam is achieved. The stabilization of the topical emulsions may be established and optimized by using the preferred combinations of hydrophilic and lipophilic emulsifiers, properly aligned at the water/oil interface. The emulsifying agents and their concentrations and proportions may be chosen according to the principle of the well-established HLB method published by W. C. Griffen ["H. L. B. - The Hydrophilic-Lipophilic Balance," J. Soc. Cos. Met. Chem., Vol. 5, p. 249 (1954)].

In the case where the composition according to the invention is an emulsion, the oil phase is selected from the group consisting of beeswax, spermaceti, 2-octyl dodecanol, lanolin, sodium $C_{12-15}$ alcohols sulphate, esters of fatty acids and high molecular weight alcohols such as cetyl palmitate and cetearyl octanoate, esters of fatty acids and branched alcohols or polyols such as isopropyl palmitate or myristate, cocoglycerides, cosbiol, wool alcohols, cocoa butter, stearyl alcohol, cholesterol, liquid paraffin, soft paraffin, hard paraffin, or the like.

The emulsifying agents used for the purpose of dispersion of the above-mentioned fats or oils and the like in the aqueous phase are advantageously selected from the group of non-ionic surfactants consisting of sorbitan sesquioleate, PEG-5 glyceryl stearate, poloxamers, cetostearyl alcohol, polysorbate 60, sorbitan monostearate, sorbitan monooleate, and glyceryl monostearate.

In the case where the composition according to the invention is a gel or solution, the composition preferably comprises an oleic acid/oleate salt, and generally a lower alkanol having from one to four carbon atoms, water, a gelifying agent (if a gel), one or more polyhydric alcohols selected from the group consisting of a lower alkylene glycol having from two to four carbon atoms, glycerine, and polyethylene glycol, having an average molecular weight from 200 to 2000, and a base, e.g., sodium hydroxide, or an acid, e.g., citric acid, for pH adjustment.

The gelifying agents are selected from the group consisting of polysaccharides such as cellulose derivatives, acrylic polymers, proteins, polyhydroxy compounds such as polyethylene glycol having an average molecular weight from 400 to 2000, and polyoxyethylene-3-cetylstearyl alcohol, known as Emulgin B3.

All semi-solid topical preparations should preferably be stable and consistent, non-leaky, non-staining, and non-greasy.

In the case where the composition according to the present invention is a powder, the composition preferably comprises an oleic acid and/or alkali oleate, and generally a diluting powder compound suitable as a lubricant. This lubricant is selected from the group consisting of talc, microcrystalline cellulose, polyvinyl pyrrolidone, metal stearates, lactose or starch known to have non-irritating, non-toxic and inert properties.

In accordance with another aspect of the invention, the oleic acid and/or oleate salt could be topically applied in a slow-release manner using an adhesive sponge bandage, or, alternatively, a gauze or sponge sandwich containing a layer of the active principals of the invention situated between upper and lower absorbent layers.

The carboxylic/dicarboxylic acids and/or their salts of the present invention can also be applied onto the mucosa, for example, as a buccal gel or vaginal preparation. For this purpose, several bioadhesive polymers are selected from the group consisting of polyethylene glycols, cellulose derivatives, starch, and polyacrylic acid such as polycarbophil and Carbopol 934.

As described hereinbefore, the vehicles can be in the form of a cream, lotion, ointment, gel, stick, topical solution, gargle solution, foam, spray, liquid soap, or powder. From the point of view regarding the formulation characteristics, the pharmaceutical preparations could be processed as a water-in-oil or an oil-in-water emulsion, clear solution, gel solution, aerosol, powder mix, film- forming liquid, bioadhesive preparation, detergents- containing gel, suspension in gel, liquid, or emulsion, etc.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

Water-in-Oil Ointment

| Ingredient | Percent by Weight |
|---|---|
| DEHYMULS E | 7.00 |
| White beeswax | 4.00 |
| White vaseline | 20.00 |
| Heavy liquid Paraffin | 10.26 |
| Propylene glycol | 25.00 |
| Oleic acid | 0.30 |
| Sodium hydroxide | 0.44 |
| Purified water | q.s. |
| Citric acid 20% solution to pH 7.6–7.8 in aq. sol. | |

DEHYMULS E = sorbitan sesquioleate (and) penta-erythrityl tetracocoate (and) stearyl citrate (and) beeswax (and) aluminum stearate.

Emulsification is effected by heating the oil phase (ingredients 1–4) to 88 dC and blending while mixing into the aqueous phase, preheated to 75 dC. The aqueous phase is prepared by dissolution of sodium hydroxide, oleic acid, propylene glycol by sequence in purified water, followed by adjusting the pH using citric acid solution.

EXAMPLE 2

Oil-in-Water Cream

| Ingredient | Percent by Weight |
|---|---|
| ARLATONE 983 S | 6.25 |
| CUTINA CBS | 8.75 |
| Cetearyl octanoate | 3.75 |
| Propylene glycol | 38.00 |
| Oleic acid | 3.00 |
| Sodium hydroxide | 0.44 |
| Purified water | q.s. |
| Citric acid 20% solution to pH 7.6–7.8 in aq. sol. | |

ARLATONE 983 S = polyoxyethylene-5-glyceryl stearate.
CUTINA CBS = glyceryl stearate (and) cetearyl alcohol (and) cetyl palmitate (and) coco-glycerides.

The oil phase (ingredients 1–3) is heated to 80 dC while mixing until a uniform liquid is achieved. The oil phase is then added into the pre-prepared and 80 dC preheated aqueous phase (see Example 1), while mixing and homogenizing at 80 dC.

EXAMPLE 3

Oil-in-Water Cream

| Ingredient | Percent by Weight |
|---|---|
| Mineral oil | 5.00 |
| LANNETE WAX SX | 7.50 |
| Vaseline | 12.50 |
| Propylene glycol | 38.00 |
| Oleic acid | 3.00 |
| Sodium hydroxide | 0.44 |
| Purified water | q.s. |
| Citric acid 20% solution to pH 7.6–7.8 in aq. sol. | |

LANNETE WAX SX = cetearyl alcohol (and) sodium C12–15 alcohols sulphate.

The oil phase (ingredients 1–3) is heated to 80 dC while mixing until a uniform liquid is achieved. The oil phase is then added into the pre-prepared and 80 dC preheated aqueous phase (see Example 1) while mixing and homogenizing at 80 dC.

EXAMPLE 4

Water-in-Oil Cream

| Ingredient | Percent by Weight |
|---|---|
| Phase A: | |
| DRAGOSAN w/o | 8.00 |
| VESTAN-80 | 6.00 |
| Mygliol-812 | 10.00 |
| DRAGOXAT EH | 4.00 |
| Phase B: | |
| Oleic acid | 3.00 |
| Propylene glycol | 30.00 |
| Sodium hydroxide | 0.44 |
| Purified water | q.s. |
| Citric acid 20% soiution to pH 7.6–7.8 in aq. sol. | |

DRAGOSAN w/o = a mixture of sorbitan isostearate, hydrogenated castor oil, ceresin, beeswax and mineral oil.
VESTAN-80 = mineral oil.
Mygliol-812 = caprylic/capric acids.
DRAGOXAT EH = octyldodecyl octanoate.

Phase A is heated while stirring at 80 dC. Phase B is prepared as in Example 1. At 80 dC, phase B is emulsified in phase A. On cooling to 50 dC, the cream is continuously mixed and homogenized.

EXAMPLE 5

Gel Preparation

| Ingredient | Percent by Weight |
|---|---|
| Oleic acid | 4.40 |
| Sodium hydroxide | 0.64 |
| Propylene glycol | 50.00 |
| Methocel K-15 | 1.90 |
| Purified water | q.s. |
| Citric acid 20% solution to pH 7.3–7.5 in gel | |

Methocel K-15=hydroxypropyl methylcellulose

Manufacturing procedure as in preparation of aqueous phase in Example 1, followed by dissolution of the gelling agent—Methocel.

EXAMPLE 6

Foam Preparation

| Ingredient | Percent by Weight |
|---|---|
| CETIOL HE | 9.00 |
| Propylene glycol | 38.00 |
| Oleic acid | 3.00 |
| Sodium hydroxide | 0.44 |
| BRIJ 35 | 1.00 |
| ARLACEL 186 | 0.10 |
| Purified water | q.s. |
| Citric acid 20% solution to pH 7.6–7.8 in concentrate | |
| Isopropane/butane/isobutane 90:9:1 | +5–7% |

CETIOL HE=polyethylene glycol 7 glyceryl cocoate.
BRIJ 35=polyoxyethylene 23 lauryl alcohol.
ARLACEL 186=glyceryl mono and dioleate.

At ambient temperature, BRIJ 35, ARLACEL 186 and CETIOL HE are dissolved in the aqueous solution of sodium oleate preprepared according to the procedure described in Example 1 (aqueous phase). The pH is asjusted as the last step, using citric acid solution. The ready concentrate is filled into aerosol containers and sealed with valves. The propellant gas is then filled under pressure.

EXAMPLE 7

Orabase (Adhesive Oral Gel)

| Ingredient | Percent by Weight |
|---|---|
| Oleic acid | 3.00 |
| Sodium hydroxide | 0.44 |
| Ethyl alcohol | 10.00 |
| Propylene glycol | 30.00 |
| GANTREZ AN 169 (GAF) | 2.50 |
| Preservatives | 0.12 |
| Purified water | q.s. |
| Citric acid 20% solution to pH 7.6–7.8 in sol. | |

GANTREZ AN 169 (GAF) = gelling agent.

Manufacturing procedure as in preparation of aqueous phase in Example 1, followed by dissolution of the gelling agent, GANTREZ.

EXAMPLE 8

Gargle Solution

| Ingredient | Percent by Weight |
|---|---|
| Oleic acid | 3.00 |
| Sodium hydroxide | 0.44 |
| Propylene glycol | 38.00 |
| Sodium saccharine | 0.10 |
| Flavour | 0.10 |
| Purified water | q.s. |
| Citric acid 20% solution to pH 7.6–7.8 in sol. | |

Manufacturing procedure as in preparation of aqueous phase in Example 1.

EXAMPLE 9

Comparative Effectiveness of Preparations
In-Vivo Preventive Testing of Gel (Example 5) in the Topical Treatment of Experimental Cutaneous Herpes Simplex Virus Type 1 (HSV-1) Infection In a double-blind study, the efficacy of a gel (Example 5) according to the present invention was evaluated as compared to an untreated control and a drug-containing (5% acyclovir) cream, currently marketed by Burroughs-Wellcome under the trade name ZoviraxR.

A guinea pig model was selected for the cutaneous HSV-1, because the model mimics the human herpes simplex labialis infection [Hubler, et al., J. Invest. Dermatol., Vol. 62, pp. 92–95 (1974)]. Forty-eight animals (young male D. Hartly guinea pig CRL:(HA)BR strain, Charles River, U. K.) were assigned to the experiment.

The stock virus (HSV-1, HF strain) was grown on VERO cells at multiplicity of infection of 0.1. The virus was grown for three days at 37 dC and thereafter frozen and thawed three times. Then, it was cleared by two-speed centrifugation at 15,000 rpm for 15 minutes. The stock virus was then dispensed into 1 ml vials and stored at −70 dC.

The virus was inoculated intradermally on three locations on the back of each animal. The area into which the virus was to be inoculated was divided into three squares with a marking pen. In the middle of each area, about 20 microliters of HSV at a concentration of 106 PFU/ml was applied by 10 injections close to each other. In order to assign the location of the various treatments on each animal and to overcome any gradient effect, a latin-square design was used.

Treatment was started 2–3 hours after inoculation and consists of three daily applications of the topical preparations (about 50 mg) for a period of three days (9 treatments). Animals were inspected once daily, and the lesions or inoculated sites were scored in the following manner:

| Score | Description |
|---|---|
| 0.0 | No signs detected |
| 0.5 | Erythema and slight edema at the site |
| 1.0 | Erythema and one or two small vesicles |
| 2.0 | Erythema and numerous small vesicles |
| 2.5 | Numerous medium-sized vesicles |
| 3.0 | Numerous large vesicles |

In addition to the lesion scoring described above, the number of vesicles in each marked area was counted and recorded at the same time as the scoring.

Table 1 shows the mean and the standard deviation of the scores observed at days 2 and 3 from inoculation. Table 2 presents the mean vesicles quantities at days 2 and 3, and Table 3 shows the combination of the two parameters, providing a more comprehensible picture of the diseased state. The results clearly demonstrate the significant superiority of the composition of the invention over the acyclovir-containing commercial cream and the untreated control. The lowest average response at day 3 was associated with the non-drug-containing gel, followed by ZoviraxR cream, and finally untreated control. The score and number of vesicles for the untreated control areas were almost as high as the respective values of ZoviraxR cream, while those of the gel formulation were significantly lower. Thus, the responses (score and vesicles) to the gel were relatively low at day 3. In order to weight the evidence that this treatment was really better than that of the ZoviraxR cream, the difference between responses to this treatment and those observed with respect to ZoviraxR were tested for significance. The results were highly significant ($p<0.001$) for each of the responses.

TABLE 1

Mean Score Number at Each Infection Site
(Mean p S.E.)

| | Day 2 | Day 3 |
|---|---|---|
| Untreated | 2.06 (p 0.11) | 1.90 (p 0.13) |
| No-drug gel | 1.97 (p 0.12) | 0.97 (p 0.13) |
| ZoviraxR | 2.05 (p 0.09) | 1.83 (p 0.12) |

TABLE 2

Mean Count of Vesicles at Each Infection Site
(Mean p S.E.)

| | Day 2 | Day 3 |
|---|---|---|
| Untreated | 6.17 (p 0.46) | 5.83 (p 0.48) |
| No-drug gel | 4.40 (p 0.43) | 1.13 (p 0.32) |
| Zovirax ® | 5.98 (p 0.43) | 5.17 (p 0.46) |

TABLE 3

Mean of Combined Parameters (Score X Vesicles)
at Each Infection Site
(Mean p S.E.)

| | Day 2 | Day 3 |
|---|---|---|
| Untreated | 14.48 (p 1.19) | 13.58 (p 1.18) |
| No-drug gel | 10.08 (p 1.02) | 2.47 (p 0.75) |
| Zovirax ® | 13.40 (p 1.04) | 11.30 (p 1.16) |

EXAMPLE 10

In order to further demonstrate the unique ability of fatty acid as salts to penetrate through the skin and to deliver other antiviral drugs, two comparisons between formulations were performed:

(a) a comparison between two gel formulations containing 5% (micellar form) and 10 % (coacervate) of oleic acid/sodium oleate combination to deliver acyclovir through skin. The comparison was accompanied with testing of Zovirax cream, a commercial product not containing fatty acid salts. Apart from the fact that the two oleate containing preparations proved to be superior than that of the reference product, it has been found that 10% oleic/oleate product decreases the penetration, compared to the 5% oleate product. The decrease in the amount permeated can be explained only if we can understand the mechanism by which oleic acid enhances the skin penetration. It has been published by Francoeur et al (Pharm. Res., vol 7, pp. 621–627, 1990) that "oleic acid selectively perturbs the inherent lipid structure of the stratum corneum, reducing the transition temperatures and cooperatively associated with their phase properties". The enhanced transport of molecules through these interfacial defects may require water. Water is needed to deliver more solubilized fatty acid salts deeper into the skin. Increase in oleate in the gel vehicle which may be much higher than the critical micellization concentration (CMC), results in coacervation, less water availability and decrease in solubilization of oleate and/or drug molecules. (See FIG. 1).

| | Percentage in Formulation | |
|---|---|---|
| Ingredient | AGD-52 | AGD-53 |
| Sodium oleate | 5.0 | 10.0 |
| Methocel K-15M | 1.5 | 1.5 |
| Nipagin | 0.1 | 0.1 |
| Nipasol | 0.02 | 0.02 |
| Propylene glycol | 50.0 | 50.0 |
| Citric acid 20% sol. | 3.2 | 4.4 |
| Acyclovir | 5.0 | 5.0 |
| Water, up to: | 100% | 100% |

Figure 2:
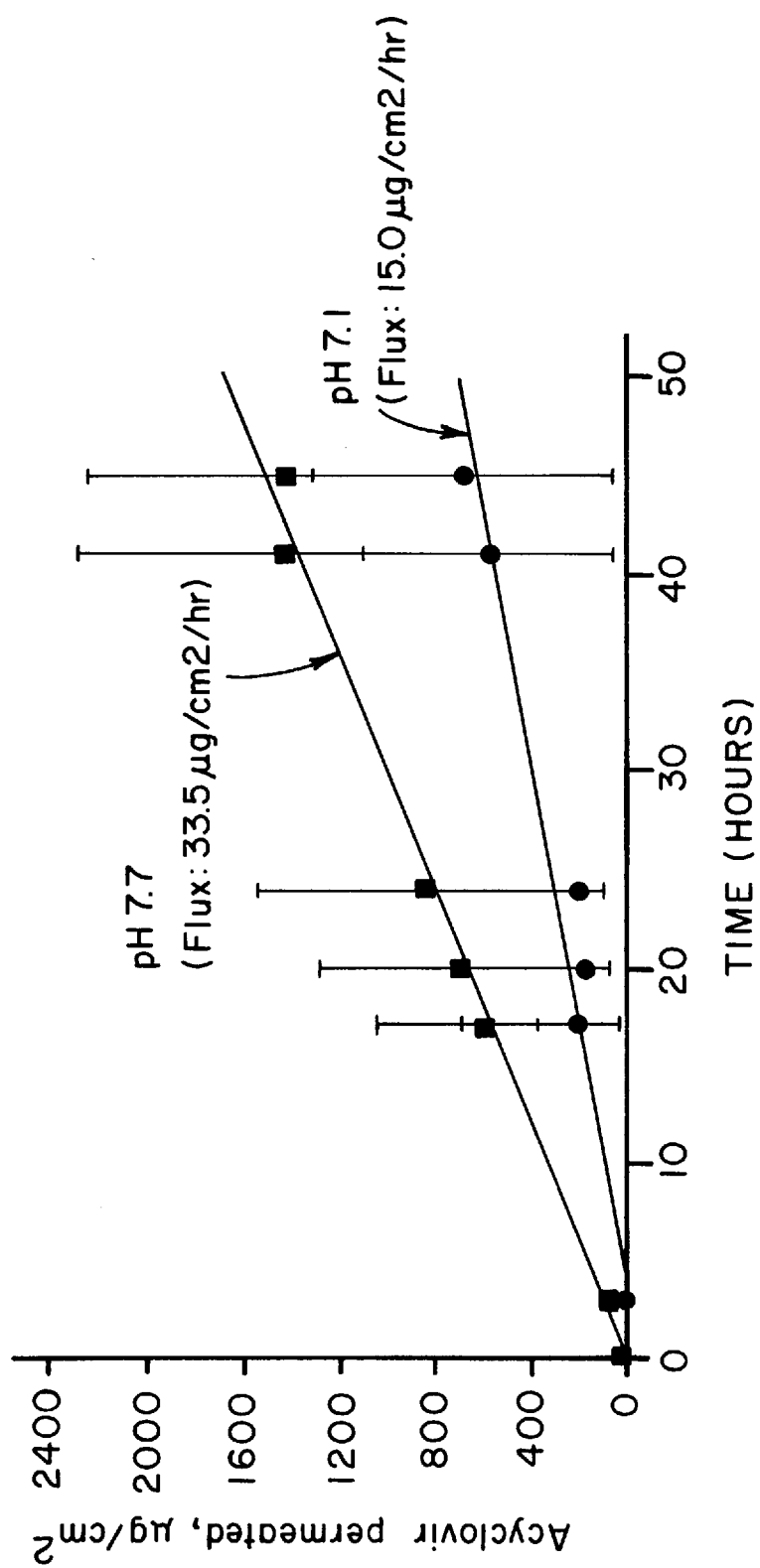
FIG. 2 is a graphic illustration of the transdermal permeation of acyclovir in nude mice as a function of time following administration of two different acyclovir formulations having different pHs.

(b) a comparison was made between two formulations at different pH values, in the range where one formulation contained significantly higher levels of sodium oleate than the other formulation. Both formulations contained 5% oleic/oleate calculated as oleic acid. By using pH 7.1, 10%–20% of the total oleic acid is in the form of a salt, while a rise in the pH to 7.7 increases the salts to almost 100 %. FIG. 2 shows surprisingly that the salt form is preferred over the free acid in delivering molecules into the skin, said salt form characterized by a better and more consistent permeation of the fatty acid salts to the deeper strata of the skin. It has been postulated that the oleate salts stabilize the micellar system by increasing the zeta potential and preventing coacervation. This phenomenon, together with the profound effect on herpes lesions, demonstrates the superiority of the new composition of the present invention over other non-hydrophilic compositions known in the art.

| | Percentage in Formulation | |
|---|---|---|
| Ingredient | F-1 | F-2 |
| Oleic Acid | 4.4 | 4.4 |
| NaOH 10% sol. | 0.64 | 0.64 |
| Methocel K-15M | 1.9 | 1.9 |
| Nipagin | 0.1 | 0.1 |
| Nipasol | 0.02 | 0.02 |
| Propylene glycol | 50.0 | 50.0 |
| Citric acid 20% sol. | To pH 7.1 | to pH 7.7 |
| Acyclovir | 5.0 | 5.0 |
| Water, up to: | 100% | 100% |

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A method for the treatment of pre-existing lesions and sores of the skin or mucosa associated with a herpes virus and for prevention of future lesions and sores of the skin or mucosa associated with a herpes virus, comprising administering a topical pharmaceutical composition, consisting essentially of an alkali oleate as active ingredient therein, in an effective amount for the treatment of lesions and sores of the skin or mucosa, in combination with a pharmaceutically or cosmetically acceptable carrier.

* * * * *

UNITED STATES PATENT AND TRADEMARK OFFICE
CERTIFICATE OF CORRECTION

PATENT NO. : 5,869,529
DATED : February 9, 1999
INVENTOR(S) : Amnon SINTOV

It is certified that error appears in the above-identified patent and that said Letters Patent is hereby corrected as shown below:

On the title page, item [75], Inventors, change "BEER-SHAVA" to --BEER-SHEVA--.

Signed and Sealed this

Twenty-ninth Day of June, 1999

Attest:

Q. TODD DICKINSON

Attesting Officer       Acting Commissioner of Patents and Trademarks